(12) United States Patent
Ricotti et al.

(10) Patent No.: US 9,415,163 B2
(45) Date of Patent: Aug. 16, 2016

(54) SYSTEM FOR CONTROLLED ADMINISTRATION OF A SUBSTANCE FROM A HUMAN BODY-IMPLANTED INFUSION DEVICE

(75) Inventors: Leonardo Ricotti, Volterra (IT); Tareq Assaf, Genoa (IT); Cesare Stefanini, Vicopisano (IT); Arianna Menciassi, Pontedera (IT)

(73) Assignee: SCUOLA SUPERIORE DI STUDI UNIVERSITARI E DI PERFEZIONAMENTO SANT'ANNA, Pisa (IT)

( * ) Notice: Subject to any disclaimer, the term of this patent is extended or adjusted under 35 U.S.C. 154(b) by 742 days.

(21) Appl. No.: 13/809,580

(22) PCT Filed: Jul. 20, 2010

(86) PCT No.: PCT/IT2010/000319
§ 371 (c)(1),
(2), (4) Date: Jan. 28, 2013

(87) PCT Pub. No.: WO2012/011132
PCT Pub. Date: Jan. 26, 2012

(65) Prior Publication Data
US 2013/0116667 A1 May 9, 2013

(51) Int. Cl.
*A61M 5/172* (2006.01)
*A61M 5/142* (2006.01)
*A61M 39/04* (2006.01)

(52) U.S. Cl.
CPC ......... *A61M 5/1723* (2013.01); *A61M 5/14276* (2013.01); *A61M 39/04* (2013.01);
(Continued)

(58) Field of Classification Search
CPC .......... A61M 5/1723; A61M 5/14276; A61M 2205/3507; A61M 2205/8206; A61M 2205/502; A61M 2209/045; A61M 2209/086; A61M 39/04; A61M 2005/1726; A61M 2205/8212; A61M 2205/04
See application file for complete search history.

(56) References Cited

U.S. PATENT DOCUMENTS

2002/0156462 A1 10/2002 Stultz
2005/0055039 A1* 3/2005 Burnett ............... A61B 5/14539
606/151

(Continued)

FOREIGN PATENT DOCUMENTS

JP 2002085556 3/2002
WO 2004/014254 2/2004
WO 2010/040551 A2 4/2010

OTHER PUBLICATIONS

STIC Search. Dated Nov. 3, 2015.*

(Continued)

*Primary Examiner* — Kami A Bosworth
*Assistant Examiner* — Hamza Darb
(74) *Attorney, Agent, or Firm* — Steinfl & Bruno LLP

(57) ABSTRACT

A system for the controlled administration of a substance by means of an infusion device implanted in the human body is described. The system has an implantable unit for detecting a shortage or an excess of such substance or a physiological parameter correlatable to the shortage or excess of such substance, an infusion group of this substance implantable in the peritoneal cavity and having a central control unit for processing data received from the detection unit, and energy storage means to power such infusion group. The system also has a carrier of such substance adapted to be ingested, and a refilling device for refilling the infusion group with such substance.

16 Claims, 5 Drawing Sheets

(52) U.S. Cl.
CPC .. *A61M2205/3507* (2013.01); *A61M 2205/502* (2013.01); *A61M 2205/8206* (2013.01); *A61M 2209/045* (2013.01); *A61M 2209/086* (2013.01)

(56) References Cited

U.S. PATENT DOCUMENTS

| | | | |
|---|---|---|---|
| 2009/0112190 A1 | 4/2009 | Boyden | |
| 2010/0030024 A1* | 2/2010 | Sitte | A61B 1/00158 600/118 |

OTHER PUBLICATIONS

PCT International Search Report, Application PCT/IT2010/000319, filed Jul. 20, 2010 in the name of Scuola Superiore di Studi Universitari e di Perfezionamento Sant'Anna, Date of mailing: Apr. 21, 2011.

PCT Written Opinion of the International Searching Authority, Application PCT/IT2010/000319, filed Jul. 20, 2010 in the name of Scuola Superiore di Studi Universitari e di Perfezionamento Sant'Anna, Date of mailing: Apr. 21, 2011.

AM Albisser et al., "Clinical control of diabetes by the artificial pancreas", Diabetes, 23(5):397-404, 1974.

JL Selam, "External and implantable insulin pumps: current place in the treatment of diabetes", Exp Clin Endocrinol Diabetes, 109:333-340, 2001.

TM Gross et al., "Efficacy and reliability of the continuous glucose monitoring system", Diab Tech & Therap, 2:19-26, 2000.

SK Garg et al., "Improved glucose excursions using an implantable real-time continuous glucose sensor in adults with type 1 diabetes", Diab Care, 27(3):734-738, 2004.

R Jamali et al., "Continuous glucose monitoring system signals the occurrence of marked postprandial hyperglycemia in the elderly", Diab Tech & Therap, 7(3):509-515, 2005.

TC Dunn et al., "Rates of glucose and change measured by blood glucose meter and the glucowatch biographer during day, night, and around mealtimes", Diab Care, 27(9):2161-2165, 2004.

Renard et al., "Artificial β-cell: clinical experience toward an implantable closed-loop insulin delivery system", Diab & Metab, 32(5):497-502, 2006.

Report of Medtronic's presentation of the Paradigm Veo System at the annual meeting of the International Society for Pediatric and Adolescent Diabetes (ISPAD) in Ljubljana, Slovenia, Sep. 2009.

\* cited by examiner

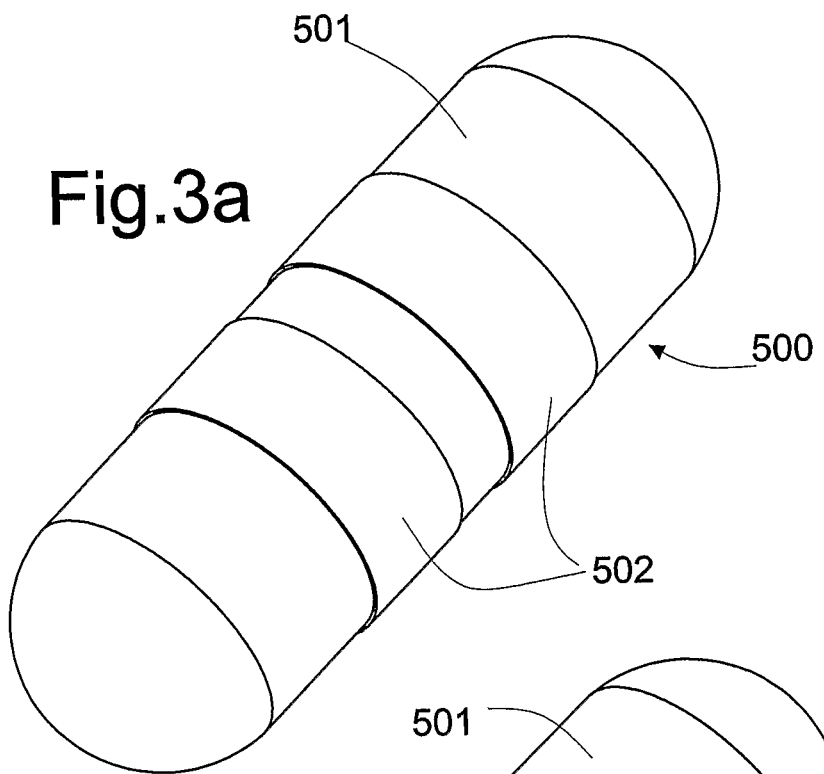
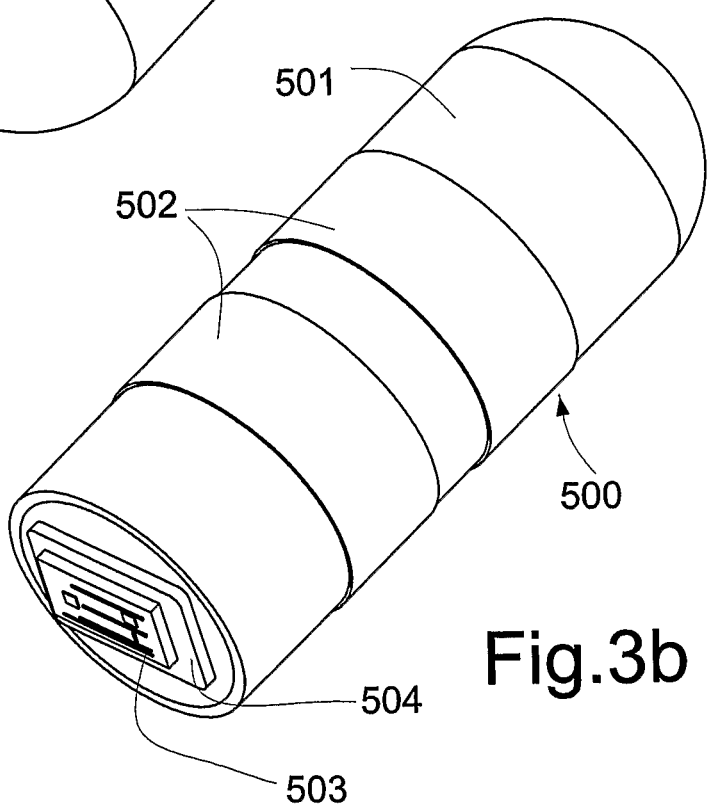

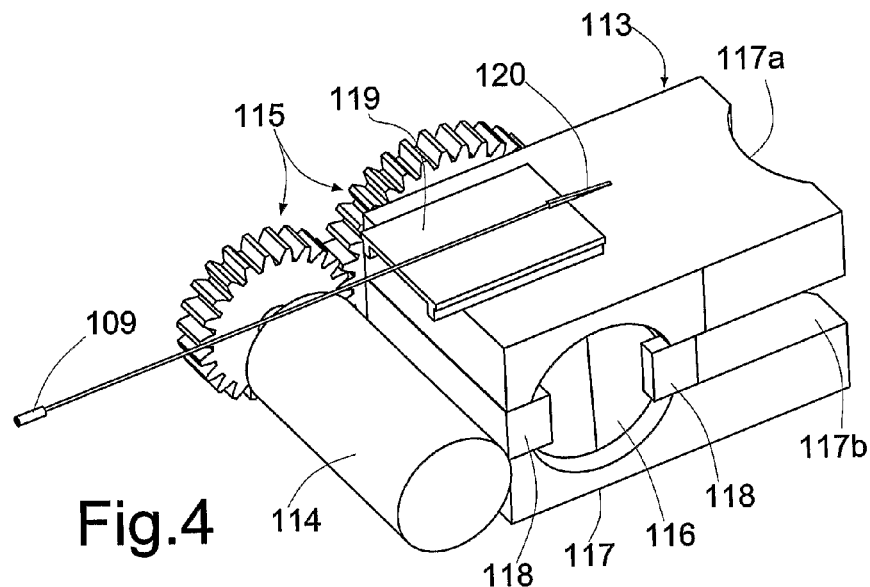
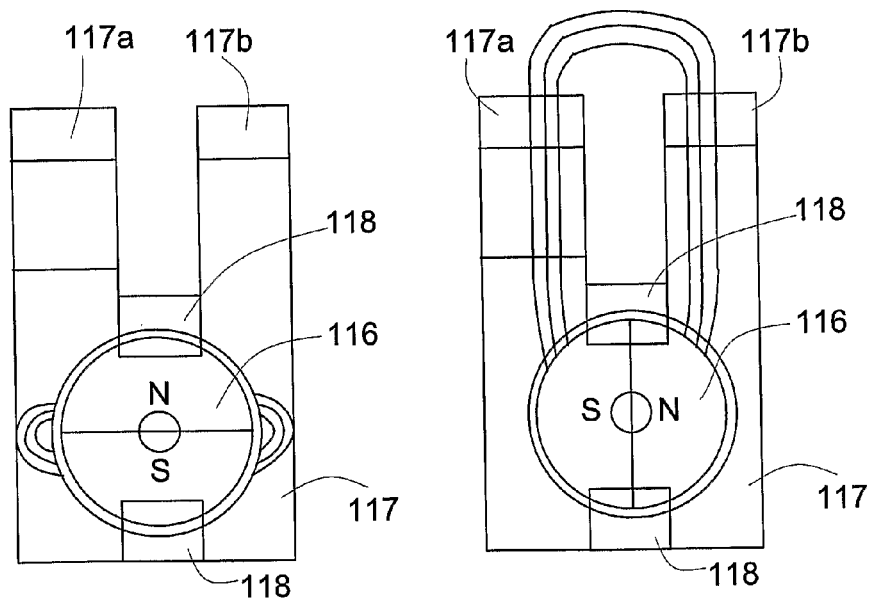

SYSTEM FOR CONTROLLED ADMINISTRATION OF A SUBSTANCE FROM A HUMAN BODY-IMPLANTED INFUSION DEVICE

CROSS REFERENCE TO RELATED APPLICATIONS

The present application is the US national stage of International Application PCT/IT2010/000319 filed on Jul. 20, 2010.

FIELD OF THE INVENTION

The present invention generally regards the controlled administration of substances through infusion devices implanted in the human body and more particularly has as object a system for the controlled administration of a substance such as a drug, a hormone or a hormone complex and the like for which other administration modes result unsatisfactory or ineffective.

STATE OF THE ART

Pathological conditions are known which require extended administration over time (also over the entire life of the patient) of substances adapted to compensate for the shortage or absence of those normally produced endogenously, or adapted to supply active principles against chronic diseases. Such administration occurs through infusion devices that are partially or totally implanted in the human body. For example, a pathological condition which requires this type of treatment is diabetes.

Many diabetes types are currently known. The main ones are

Type 1
Type 2
Gestational Diabetes

Diabetes mellitus type 1 is characterized by a shortage of insulin production by the beta cells of the Islets of Langerhans in the pancreas, often due to the destruction of these cells following an autoimmune attack by T lymphocytes. Currently, practically all the individuals who suffer diabetes mellitus type 1 must be subjected to daily injections of exogenous insulin, which constitute the most widespread and common remedy but which considerably limit the possibility of diabetes subjects to live a normal life. Non-insulin treatments, based on monoclonal antibodies and stem cell treatments, are effective on animal models, but have not yet passed the clinical trial phase on human individuals. Type 2 diabetes is characterized by an increase of the glycemia in the blood due to a double effect: that of insulin-resistance and that of a deficit of insulin secretion. These two effects can coexist, or they can present themselves separately and/or subsequently. Gestational diabetes is present in certain subjects during pregnancy and causes hyperglycemia due to the incapacity of the maternal pancreas to secrete a sufficient amount of insulin to oppose the effect of the hormones produced by the placenta, which have an opposite effect with respect to insulin itself.

In order to allow diabetic patients to automatically control their glucose level in the blood, it was proposed to substitute the endocrine functionality of the natural pancreas with a device generally known as artificial pancreas. The medical introduction of the artificial pancreas is relatively recent (A M Albisser et al.: Clinical control of diabetes by the artificial pancreas, *Diabetes*, 23(5):397-404, 1974), but up to now a long-term implantable system has not been identified. There are fairly complete and advanced devices in the literature which attempt to confront this technological problem, but no solution at the moment appears resolutive.

An important element of an implantable pancreas is the pump for the release of insulin. Among the various types of pumps and their different implant locations, the most interesting are those which release insulin in the peritoneal cavity, reaching the portal vein. From here, the insulin immediately stops the hepatic production of glucose, effectively emulating the functionality of the beta cells in controlling glycemia. This technological problem was resolved and the first implantable insulin pump prototype appeared in Europe in 2000. The insulin reserve is sufficient for 3 months, after which the device is explanted and resupplied with insulin, as well as new batteries (J L Selam: External and implantable insulin pumps: current place in the treatment of diabetes, *Exp Clin Endocrinol Diabetes*, 109:333-340, 2001). On the basis of this device, other more sophisticated pumps were developed, but they too must be periodically resupplied, making their long-term implantation impossible. An infusion pump of this type was placed on the market by Minimed (USA). This pump is made of titanium and has a weight of 150 g, releases insulin in the peritoneal cavity and is remotely controlled by the patient. The tank has a capacity of 15 ml and must be periodically refilled by means of transcutaneous insulin injections, an invasive and irritating procedure which the user has a hard time accepting.

Recently, much more advanced prototypes and commercial products provide for the coupling of external insulin pumps with a transcutaneous catheter, coupled with advanced glycemic sensors (implanted or otherwise) and with advanced control algorithms. Such systems, even if considerably improved from the standpoint of the glycemia monitoring and insulin release control, have not solved the problem of long-term implantability.

In substance, the problem is how to resupply the insulin and energy device without having to surgically operate on the patient. An adequate solution has not yet been found for this problem. In addition, none of the known devices is completely mini-invasive: the presence of catheters or other transcutaneous structures naturally limit the freedom of movement and life of the user.

An important element for making an autonomous device is the presence of a glycemic sensor which continuously supplies data relative to the concentration of glucose in the blood. Notwithstanding the intrinsic technical difficulties associated, numerous systems exist today for the continuous monitoring of the glycemia.

Such systems continuously measure the glucose concentration in the interstitial fluids, through needle-shape sensors (T M Gross et al.: Efficacy and reliability of the continuous glucose monitoring system, *Diab Tech & Therap*, 2:19-26, 2000; S K Garg et al.: Improved glucose excursions using an implantable real-time continuous glucose sensor in adults with type 1 diabetes, *Diab Care*, 27(3):734-738, 2004; R Jamali et al.: Continuous glucose monitoring system signals the occurrence of marked postprandial hyperglycemia in the elderly, *Diab Tech & Therap*, 7(3):509-515, 2005) or through a micro-dialytic fiber (T C Dunn et al.: Rates of glucose and change measured by blood glucose meter and the glucowatch biographer during day, night, and around mealtimes, *Diab care*, 27(9):2161-2165, 2004). The supposition that the glucose concentration in the interstitial liquids is comparable to that of the hematic side is assumed to be well-grounded. The lag time for the balancing between the two compartments has been estimated to be around 4-10 minutes. In order to have more reliable glycemic data, above all in real time, it is necessary to employ implantable sensors which detect the data directly from the blood flow.

An ideal artificial pancreas model should combine the most physiological insulin infusion mode with the most accurate glycemia monitoring system, characterized by the least lag time. The insulin infusion which allows best imitating the function of the beta cell is undoubtedly intraperitoneal insulin infusion (IIP). The advantages of IIP are due to the release of insulin directly into the peritoneal cavity, which allows quickly reaching the portal circulation and hence reproducing physiological insulinization conditions.

It was also shown that the glucose monitoring system characterized by the shortest lag time is the subcutaneous continuous monitoring system of the glycemia and not the intravascular monitoring of the glucose.

An implantable closed-loop system MIP-XS has been proposed in the literature (Renard et al.: Artificial β-cell: clinical experience toward an implantable closed-loop insulin delivery system, *Diab & Metab*, 32(5):497-502, 2006). The system comprises a pump and a catheter for the insulin release, a glycemic sensor connected to the pump and an integrated control algorithm. An external device is capable of receiving the data. Nevertheless, also in this system it is not possible to resupply the insulin tank and the batteries from the outside.

Recently (September 2009), Medtronic presented a new device, called "Paradigm Veo System", at the annual meeting of the International Society for Pediatric and Adolescent Diabetes (ISPAD). Such device is capable of automatically suspending the insulin release when the glucose levels fall below a threshold fixed by the user. The device comprises a pump for the insulin and a continuous monitoring system of the glucose levels (by means of a sensor and a transmitter). The patient reads the glycemic progressions directly on the monitor and occasionally checks them by using the glycemia measurement strips, then he/she programs the micro-infuser to release the appropriate amount of insulin. However, if the data transmitted by the sensor show that the glucose levels have fallen below a limit fixed by the patient, the device emits an alarm signal, and if this alarm is ignored, the insulin pump automatically blocks the release of insulin up to a maximum of two hours. However, neither does this system provide for a system that is totally implantable and of long duration.

Artificial pancreas structures are for example described in WO2004/014254, and JP2002085556.

The object of the present invention is to provide a system for the controlled administration of a substance through an infusion device implanted in the human body which solves the problems encountered in the prior art and does not require surgical operations for carrying out periodical resupplying of the substance to be administered or the substitution of the batteries which supply power to the device.

One particular object of the present invention is to provide a system of the abovementioned type applied to the treatment of diabetes.

Another object of the present invention is to provide a system of the abovementioned type in which the resupplying of the substance to be administered is carried out by means of ingestion of a carrier containing a pre-established volume of said substance.

A further object of the present invention is to provide a system of the abovementioned type in which the energy recharging of the battery which supplies power to the device is carried out from the outside, in a non-invasive manner.

Another object of the present invention is to provide an intelligent carrier of the substance to be administered, suitable for being ingested, in order to transport the substance to the implant site and transfer it to the infuser device.

SUMMARY OF THE INVENTION

These and other objects are achieved with the system for the controlled administration of a substance according to the present invention whose essential characteristics are reported in claim 1.

Other important characteristics are reported in the dependent claims.

According to one aspect of the invention, a system is provided for the controlled administration of a substance via an infusion device implanted in the human body, comprising an implantable unit for detecting a shortage or an excess of the substance, an infusion group of this substance implantable in the peritoneal cavity and comprising a central control unit for processing data received by the detection unit in order to generate command signals for the release of the substance in the intraperitoneal cavity, as well as energy storage means for powering the infusion group. The system also comprises a carrier of the substance adapted to be ingested in order to passively reach the duodenal lumen and made of perforable material resistant to gastric acids, with parts made of magnetizable metal, and a recharge device for resupplying said substance to said infusion group comprising a magnetic reversible docking group for said carrier facing on the duodenal lumen and actuable when the carrier reaches a predetermined distance therefrom, and means for drawing the substance from the carrier communicating with suction means of the infusion group.

According to another aspect of the invention, an ingestible device is provided for transporting a substance to a site of the gastrointestinal tract where an infusion device of said substance is implanted, comprising a body made of gastro-resistant material and perforable, defining a chamber within which the substance is stored, means sensitive to an attraction force generated by a magnetic field arranged on the body surface and means for generating a proximity signal adapted to provide an indication on its distance from the infusion device.

BRIEF DESCRIPTION OF THE DRAWINGS

Further characteristics and advantages of the system for the controlled administration of a substance according to the present invention will be apparent from the following description of an exemplifying and non-limiting embodiment thereof, made with reference to the attached drawings in which:

FIGS. 3a and 3b illustrate an insulin capsule employed in the system according to the invention, with an end cap removed shown in FIG. 3b;

FIG. 4 shows an implantable docking device for the insulin capsule of FIGS. 3a,b;

FIGS. 6a, 6b illustrate the deactivated and activated condition, respectively, of the docking device of FIG. 4.

DETAILED DESCRIPTION OF THE INVENTION

In the following detailed description of the invention, reference is made to the case in which the substance to be administered in a controlled manner is insulin, but it is clear that the described system is also applicable when a substance of different type has to be administered.

Figure 1:
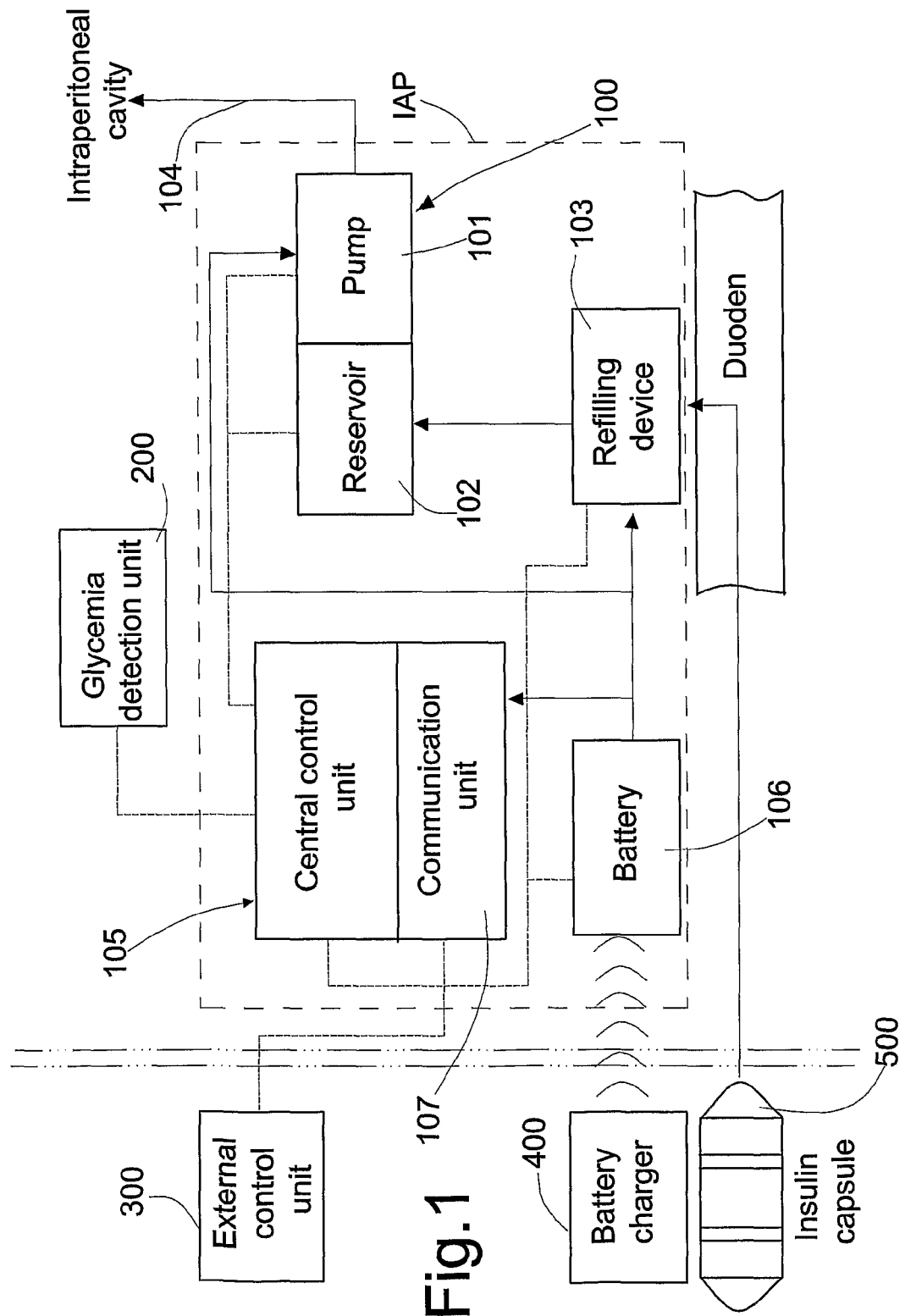
FIG. 1 illustrates the general architecture of the system for the controlled administration of insulin according to the present invention.

With reference to FIG. 1, the system for the controlled administration of insulin according to the present invention comprises an infusion group 100 comprising a pump 101 for the infusion of the insulin into the peritoneal cavity and an insulin tank 102 communicating with said pump, and an insulin refilling device 103 for the periodic resupplying the tank 102 with insulin. An outlet duct 104 extends from the pump 101 and leads into the intraperitoneal cavity for the insulin delivery. The infusion group 100 also comprises a central control unit 105 for controlling the functioning of the infusion group 100 and a main battery 106 which provides the necessary power for the functioning of the infusion group 100, the refilling device 103 and the central control unit 105. The central control unit 105 also comprises a wireless communication unit 107 (e.g. of ZigBee type or RFID type). The infusion device 100 with the relevant central control unit 105 and the battery 106, together with the refilling device 103, form a miniaturized mechatronic unit, indicated with IAP (Implantable Artificial Pancreas) in FIG. 1, implantable in the peritoneal zone, behind the stomach and near the duodenum, in substitution of, or close to, the endocrine part of the original pancreas, preferably by means of a laparoscopic operation.

The infusion group 100 cooperates with a glycemia sensor 200, also implanted, which continuously transmits the detected glycemia rate data to the central control unit 105. A wireless communication from central control unit 105 to an external control unit 300, preferably of portable type, is provided.

The system also comprises an external battery-charger 400, e.g. mounted on a belt or other wearable support, for the periodic wireless recharging of the battery 106 and a swallowable insulin carrier 500, for example a capsule containing insulin, adapted to periodically transport an insulin refill from the outside to the infusion group 100.

Figure 2:
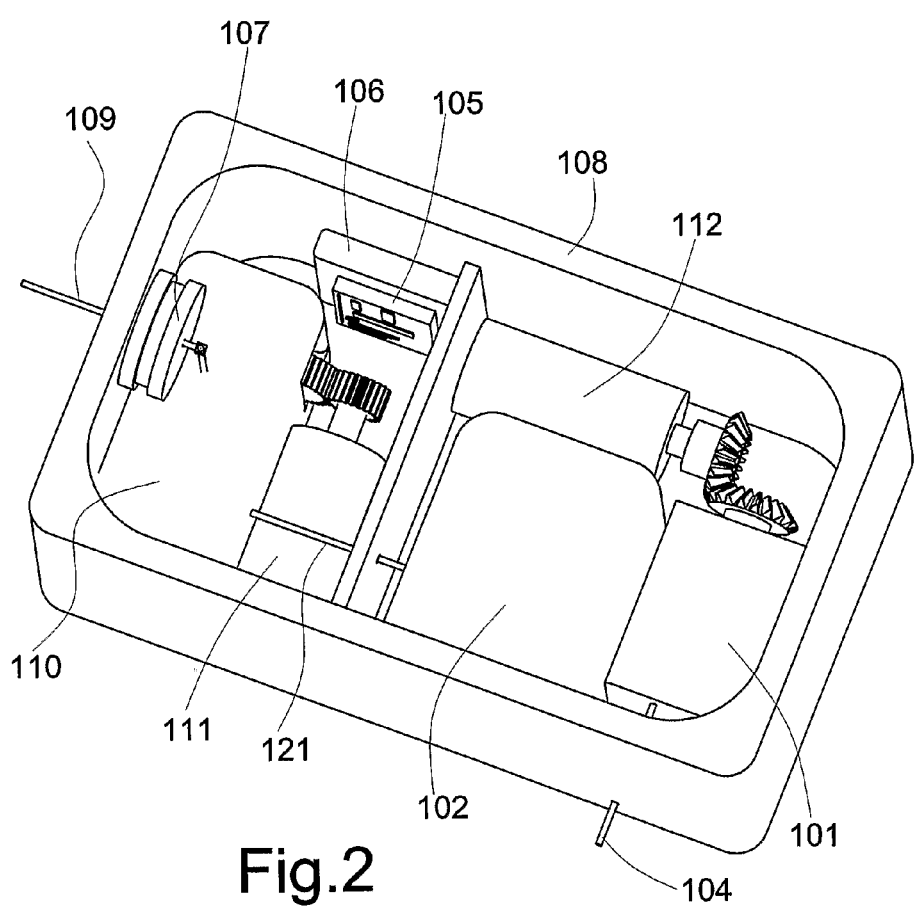
FIG. 2 schematically shows an implantable insulin infusion group employed in the system according to the present invention.

The implantable unit IAP is schematically shown in FIGS. 2 and 4. It is implanted and surgically fixed in the anatomic zone of the pancreas; it therefore physically as well as functionally substitutes this organ. Alternatively, it can be positioned close to the organ, if the latter still has residual functions.

As shown in FIG. 2, the infusion group 100, the central control unit 105 and the main battery 106 are arranged in a closed and sterile casing 108. An inlet duct 109 exits from the casing 108 to be connected with the insulin refilling device 103, described below. The duct 109 passes through a filter 107, e.g. with 0.2 micron pores, which sterilizes the insulin entering into a vacuum pump 110, actuable by a motor 111. In FIG. 2, the central control unit 105 is also shown along with the main battery 106, which respectively control and power all the actuators of the system.

From the vacuum pump 110, the insulin is transferred to the tank 102 by means of an inner duct 121 and from here to the pump 101 for the controlled release of the insulin, whose motor 112 is activated by the central control unit 105 only when the implanted glucose sensor 200 signals a glycemic rate greater than a pre-established value. Before the insertion in the peritoneal cavity through the duct 104, the insulin passes through a further filter, not shown, for the complete sterilization, essential for avoiding any risk of anaphylactic shock.

The outlet duct 104 exiting from the infusion pump 101 is an artificial channel which allows the connection of the infusion device 100 with the peritoneal cavity and is constituted by a small tube which is at least externally covered by a biocompatible material (e.g. silicone). The inlet duct 109 is connected to a needle 120 (means for drawing a substance), shown in FIGS. 4 and 5, intended to cross the duodenal wall at an orifice provided with a unidirectional (non-return) valve 123, shown in FIG. 5, surgically inserted and sutured on the wall of the duodenum, once the refilling device 103 (described below) has begun the procedure for connecting with the insulin capsule 500.

The glycemia detection unit 200 comprises an implanted subcutaneous glycemia sensor, for example the CGMS Gold of Medtronic Minimed, Inc. (USA), capable of continuously monitoring the rate of glucose present in the interstitial fluids, and a wireless communication system (RFID or ZigBee), assisted by a local battery, for the transmission of the information from the sensor to the central control unit 105.

According to the present invention, in order to periodically refill the implanted tank 102 with insulin, the use of an intelligent insulin carrier 500 is provided, e.g. in the form of a capsule containing an insulin refill, which, once ingested by the patient, travels through the digestive tract passively, i.e. without its own locomotion means, until it arrives at the duodenum, where it reaches the refilling device 103 of the implanted tank 102.

As shown in FIG. 3a, the insulin capsule 500 is formed by a substantially cylindrical body 501 delimiting an internal chamber, within which the insulin is stored. In particular, the capsule has a diameter not greater than 15 mm and length not greater than 25 mm. The capsule is made of polymer material resistant to gastric acids, but mechanically yielding in a manner such that it can be easily perforated by the refilling device 103. On the body 501 two metal rings 502 are provided for, possibly covered by a layer of the same polymer material for improving the biocompatibility, since the metal, directly in contact with the body fluids, could release ions. As shown in FIG. 3b, inside the capsule 500, a wireless communication device 503 is housed, such as a RFID tag, associated with a local battery 504, adapted to communicate continuously its own distance to another analogous receiving device of the central control unit.

The refilling device 103 comprises a docking group 113 which surfaces inside the duodenum and the needle 120 supported by the group 113 in an axially movable manner for the perforation of the housing 501 of the insulin capsule 500.

As shown in FIG. 4, the docking group 113 comprises a motor 114, preferably a stepping motor, encoder-controlled, connected via a gear transmission 115 to a magnet 116 with lateral magnetization inserted in a ferromagnetic housing 117 including two elements 118 of non-ferromagnetic material which interrupt its continuity. The magnet 116 is connected to one of the gears 115 by means of a shaft, not shown, that permits it to rotate following the activation of the motor 114. The ferromagnetic housing 117 has two pole pieces 117a and 117b whose ends are facing inside the duodenal lumen.

The magnet 116 is arranged between the two non-ferromagnetic elements 118, so that when the poles of the magnet are turned towards them, as shown in FIG. 4, the field lines are shut from north to south (FIG. 6a, deactivated condition) on a short path passing through the close ferromagnetic material, and there are no magnetic field lines outside. By rotating the magnet 116 by 90°, its poles are separated from the two non-ferromagnetic elements 118, through which the magnetic field lines cannot pass. The preferential path then becomes the longer path through the ferromagnetic part of the housing 117 (FIG. 6b, activated condition) and this results in a corresponding polarization of the ends 117a and 117b facing in the duodenal lumen.

Figure 5A:
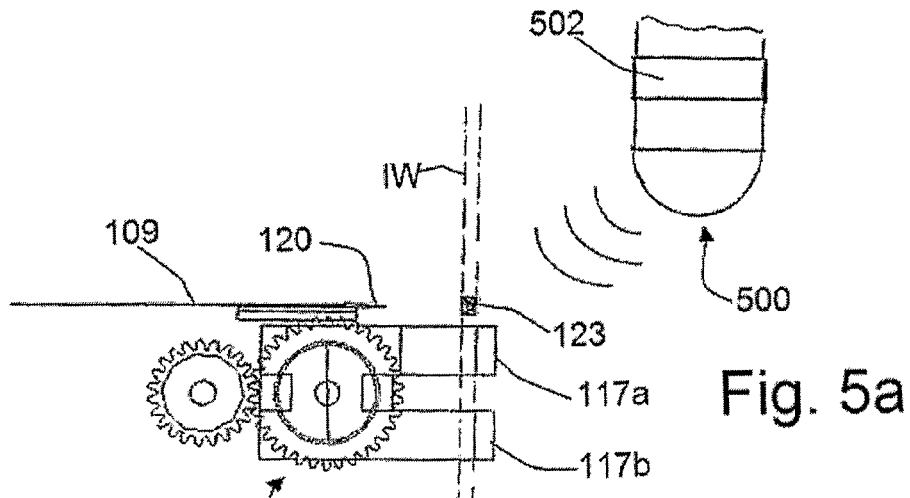
FIGS. 5a, 5b, 5c illustrate the steps of approach, docking, and release of the insulin capsule of FIGS. 3a,b.
Figure 5B:
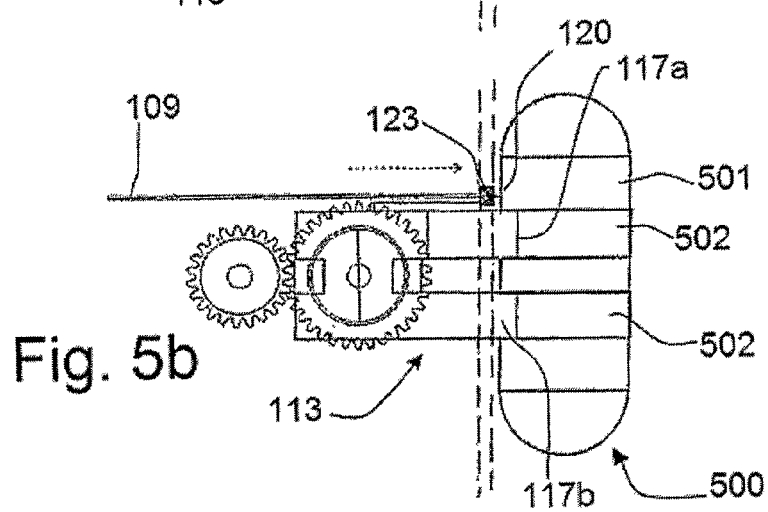
Figure 5C:
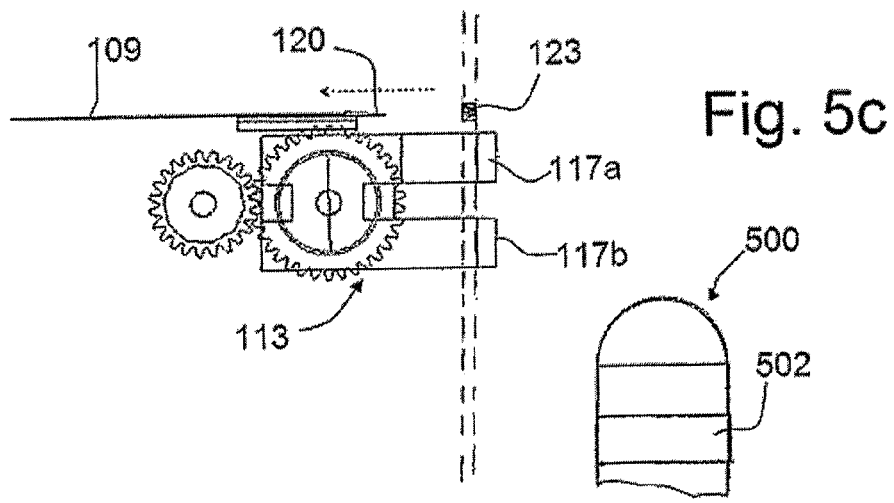

With reference to FIGS. 5a, 5b and 5c, when the insulin capsule 500 reaches the duodenal lumen, approaching the point where the infusion group 100 is implanted, it transmits a position signal through its wireless communication device 503 to the central control unit 105. The latter commands the activation of the docking group 113, after which the motor 114 imparts a rotation of 90° to the magnet 116 and a magnetic field is established at the ends 117a and 117b of the housing 117. The magnetic field attracts the insulin capsule 500 thereto due to the presence of the two metal rings 502 on its body 501. Advantageously, the ends 117a and 117b have form complementary to the ends of the capsule, in a manner so as to receive the capsule and keep it in position due to the magnetic attraction force on the metal rings 502 of the capsule. In particular, the two ends have a hollowed form with radius substantially equal to that of the body 501.

On the housing 117 of the docking device a linear motor 119 is arranged, adapted to move the needle 120 axially following a command received by the central control unit 105, after the capsule 500 has attached itself to the docking group 113. The success of the docking operation is monitored by contact sensors (not shown) present on the ends 117a and 117b, which communicate to the central unit 105 that the docking has taken place. The needle 120 is in communication with the vacuum pump 110 through the duct 109 connected to the vacuum pump 110. During its advancement, the needle 120 crosses through the intestinal wall, indicated with IW in the FIGS. 5a,b,c, at the unidirectional valve 123 sutured on the intestinal wall which prevents the reflux of liquids or solids from the intestinal lumen towards the interior of the peritoneal cavity. When the needle 120 has perforated the body 501 of the capsule 500, the central unit 105 activates the vacuum pump 110 by means of the motor 111 and the insulin contained in the capsule is transferred into the tank 102 (FIG. 5b). Once the transfer of the insulin is completed, for example signaled by a level sensor in the tank, the needle is extracted and returns to the initial position, the unidirectional valve is consequently closed and the magnet is deactivated, allowing the separation of the capsule which can continue on its path in the digestive tract (FIG. 5c) until its expulsion.

The main battery 106, like the local battery of the glycemia detection unit 200, is provided with a wireless recharge system of substantially known type based on the principles of electromagnetic induction, externally activable via coupling of suitable solenoids or similar structures. In particular, lithium polymer batteries or lithium ion batteries are employed. The recharge device 400 is configured for being positioned close to the implanted organ by attaching it, for example, to a belt or another wearable support.

The central control unit 105 processes the data coming from the glycemic sensor 200 and commands the release of a proper amount of insulin at a certain speed into the intraperitoneal cavity, the object being that of imitating the functionality of the healthy pancreatic beta cells as best as possible. The control algorithm employed is based on the proportional, integral and derivative scheme (PID) or on algorithms derived therefrom.

The amount of insulin to be infused, provided by the controller of PID type, is described by the equation:

$$PID(t) = K_P(G - G_B) + K_I \int (G - G_B) dt + K_D \frac{dG}{dt}$$

The parameters $K_P$, $K_I$, and $K_D$ are respectively the proportional, integral and derivative coefficients, and $G$ and $G_B$ represent the current glycemia and the basal glycemia. The derivative component produces the typical response of the first phase of the pancreatic beta cells, while the integral component produces the second phase.

The central control unit also provides for the monitoring of the insulin level present in the tank 102 of the infusion group 100 and the residual battery level, and transmits this information to the external control unit 300 in a wireless manner through its communication unit 107.

The external control unit 300 is preferably of portable type, and more preferably wearable, like a watch. It receives signals and data from the glycemia detection unit 200 and from the implanted central control unit 300 and comprises a display on which the glycemia level and the operations performed by the system to correct it (e.g. intraperitoneal infusion of a certain amount of insulin at a given instant) are shown in real time. The display also provides the indication of the insulin level present in the tank 102 and the residual battery level.

The external control unit also comprises an alarm device to alert the patient when the insulin volume falls below a certain threshold, and it is therefore time to ingest a capsule to refill the tank, or when the battery requires recharging. An internet connection may also be provided for in the external control unit for sending these signals to the attending physician or directly to the hospital, which is alerted and begins preparing the necessary operations for battery recharging or necessary insulin capsule refilling.

The components of the system are mainly achieved with biocompatible materials of known type, in order to assure its long-term implantability.

The system for the controlled administration of insulin according to the present invention makes available a fully artificial substitute of the natural pancreas, totally implantable in the body and biocompatible. The advantage with respect to conventional treatments, which provide for a series of daily insulin injections, is clear: the patient is not obliged to such irritating injections, which must be done at precise time intervals and which strongly condition his life. In addition, another advantage is the lower amount of insulin necessary with respect to conventional treatment, given its direct release in the peritoneal cavity, which causes a much greater absorption of the same with respect to the subcutaneous injections.

The pump 101 of the infusion group 100 releases insulin in the peritoneal cavity, simulating the functionality of the pancreatic beta cells as best as possible in controlling the glycemia. By means of intraperitoneal infusion, in fact, the pump, in addition to having a non-discontinuous infusion mode, allows the insulin to quickly reach the portal vein, and from here it immediately stops the hepatic glucose production. The particular anatomic location, moreover, allows the device a simple interfacing with the duodenum, which is found a few centimeters distant.

The few existing artificial pancreases, either partially or totally implantable, have two main defects: they either consist of parts which project outside the patient (e.g., they comprise portable apparatuses connected with small tubes which enter inside the body) or they require periodic substitutions/modifications. The first aspect strongly conditions the patient's lifestyle, since the latter is obliged to pay attention to the device at all times, making sure not to damage it. Sports activities, baths/swims etc. are limited by such factor. The second factor requires surgical operation each time the possible implanted device must be provided with new batteries or insulin. The advantages of the present invention are concentrated on these two aspects: by having an artificial pancreas that is totally implanted inside the body and in a zone protected by surrounding tissues, the patient can perform normal everyday activities, including playing sports, without worrying about the device. Such aspect is a considerable advantage, also at a psychological level and with regard to the acceptability of the device by the user. The other aspect, related to the periodic substitution/modification, is eliminated by the double solution: wireless recharge of the battery and refill of the insulin tank from outside the tank by means of ingestible capsules which transport a sufficient quantity for a prolonged use.

Even if the present invention has been described with particular reference to the case in which the substance to be administered is insulin, the case where the substance is different also falls within the scope of the present invention. In such case, the functioning of the system can be associated to a detection unit of a shortage or an excess of such substance or with the detection of a physiological parameter correlated with the shortage or excess of such substance.

Variations and/or modifications can be made to the system for the controlled administration of a substance according to the present invention, without departing from the scope of the invention as defined in the attached claims.

The invention claimed is:

1. A system for a controlled administration of a substance by means of an infusion device implanted in a human body comprising:
   an implantable unit for detecting a shortage or an excess of said substance or a physiological parameter correlatable with the shortage or the excess of said substance,
   an infusion group of said substance implantable in a peritoneal cavity and comprising a central control unit for processing data received from said implantable unit in order to generate command signals for a release of the substance in a intraperitoneal cavity,
   energy storage means for supplying power to said infusion group,
   a carrier of said substance adapted to be ingested in order to passively reach a duodenal lumen and made of a perforable material resistant to gastric acids and with parts made of magnetizable metal, and
   a refilling device for resupplying the infusion group with said substance, comprising a magnetic reversible docking group for said carrier, facing on the duodenal lumen and actuable when said carrier reaches a pre-established distance therefrom, and drawing means for drawing said substance from said carrier communicating with suction means of said infusion group.

2. The system according to claim 1, wherein said substance is insulin and said implantable unit comprises a glycemia sensor.

3. The system according to claim 2, wherein said carrier is a capsule made of biocompatible polymer material containing insulin, on which at least two magnetizable metal rings are arranged, said carrier also comprising means for a wireless communication of its position to said central control unit.

4. The system according to claim 2, wherein said glycemia sensor comprises a subcutaneous implant.

5. The system according to claim 1, wherein said magnetic reversible docking group comprises two pole pieces made of ferromagnetic material, between which a magnet with lateral magnetization is arranged, said two pole pieces being separated by two elements made of non-ferromagnetic material flanking said magnet on diametrically opposite sides, said magnet being adapted to complete a rotation of 90° around its axis to pass from a deactivated condition of said magnetic reversible docking group, in which a magnetic circuit generated by said magnet is closed inside said two pole pieces, to an activated condition, in which the magnetic circuit generated by said magnet is closed on free ends of said two pole pieces, generating a magnetic attraction force on said carrier, and vice versa.

6. The system according to claim 5, wherein said magnetic reversible docking group comprises motor means for transmitting an axial angular movement to said magnet.

7. The system according to claim 5, wherein the free ends of said two pole pieces are shaped in a complementary manner to said carrier.

8. The system according to claim 5, wherein said substance is insulin, said implantable unit comprises a glycemia sensor, and drawing means for drawing the insulin from said carrier comprise a needle adapted to penetrate said carrier, borne by a support that is movable on said two pole pieces to and from said carrier, activated when said carrier is locked on said magnetic reversible docking group.

9. The system according to claim 1, wherein said infusion group of the substance comprises a tank and an infusion pump communicating with said tank and with the duodenal lumen through a duct equipped with a non-return valve at its outlet.

10. The system according to claim 1, wherein said energy storage means comprise a battery rechargeable in a wireless manner by means of an external recharge device.

11. The system according to claim 10, wherein said external recharge device is mounted on a wearable support.

12. The system according to claim 1 further comprising a portable external control unit, communicating with said central control unit through a wireless communication unit integrated in the wireless communication unit.

13. The system according to claim 12, wherein said portable external control unit is mounted on a wearable support and comprises a display.

14. A method for refilling a substance into an infusion group of said substance, implanted in a peritoneal cavity and comprising the refilling device and the central control unit of the system according to claim 1, the method comprising the steps of:
   ingesting the carrier of said substance of the system, said carrier being suitable for being ingested to passively reach a duodenal lumen and made of perforable material resistant to gastric acids, and with parts made of magnetizable metal,
   detecting a position of said carrier with respect to said refilling device, and when a distance between said carrier and said refilling device falls below a pre-established value, activating a magnetic docking group with two pole ends facing on said duodenal lumen in order to generate a magnetic force adapted to attract said carrier towards said two pole ends and to keep said carrier in position thereon,
   drawing the substance from said carrier by means of penetration with suctioning drawing means communicating with a tank of said infusion group, and
   detecting when said tank has been refilled in order to deactivate said magnetic docking group and release said carrier.

15. The method according to claim 14, also comprising the step of detecting a volume of a substance present in said tank, and when said volume falls below a pre-established value, ingesting said carrier.

16. The method according to claim 14, wherein said substance is insulin.

* * * * *